(12) United States Patent
Trinh et al.

(10) Patent No.: US 7,096,687 B2
(45) Date of Patent: Aug. 29, 2006

(54) NON-CONSTRICTIVE ICE BAG DEVICE

(76) Inventors: Albert Long Trinh, 8671 Creekwood La., Maineville, OH (US) 45039; David Lam Trinh, 8671 Creekwood La., Maineville, OH (US) 45039

( * ) Notice: Subject to any disclaimer, the term of this patent is extended or adjusted under 35 U.S.C. 154(b) by 225 days.

(21) Appl. No.: 10/455,885

(22) Filed: Jun. 6, 2003

(65) Prior Publication Data

US 2004/0244412 A1 Dec. 9, 2004

(51) Int. Cl.
*F25D 3/08* (2006.01)

(52) U.S. Cl. .................. 62/530; 62/259.3; 607/96; 607/112

(58) Field of Classification Search .............. 62/530, 62/259.3, 457.2, 371; 607/96, 112, 114
See application file for complete search history.

(56) References Cited

U.S. PATENT DOCUMENTS

| | | | | |
|---|---|---|---|---|
| 1,623,532 A | | 4/1927 | Dudas | |
| 2,403,676 A | | 7/1946 | Modlinski | |
| 2,595,328 A | * | 5/1952 | Bowen | ........................ 607/114 |
| 2,882,692 A | | 4/1959 | Robbins | |
| 2,898,744 A | | 8/1959 | Robbins | |
| 2,925,719 A | | 2/1960 | Robbins et al. | |
| 3,058,313 A | | 10/1962 | Robbins | |
| 3,258,065 A | * | 6/1966 | Ward | ............................ 165/46 |
| 3,296,819 A | * | 1/1967 | Grough | ...................... 62/259.3 |
| 3,338,284 A | | 8/1967 | Ausnit | |
| 3,476,102 A | * | 11/1969 | Sarnoff | ........................ 126/204 |
| 3,643,665 A | | 2/1972 | Caillouette | |
| 3,780,537 A | | 12/1973 | Spencer | |
| 3,804,077 A | * | 4/1974 | Williams | ................. 126/263.1 |
| 3,885,403 A | | 5/1975 | Spencer | |
| 3,893,834 A | | 7/1975 | Armstrong | |
| 3,950,789 A | | 4/1976 | Konz et al. | |
| 4,033,354 A | | 7/1977 | De Rosa | |
| 4,218,781 A | * | 8/1980 | Lieberman | ...................... 2/247 |
| 4,263,079 A | | 4/1981 | Sutrina et al. | |
| 4,363,345 A | | 12/1982 | Scheibner | |
| 4,530,220 A | * | 7/1985 | Nambu et al. | ................. 62/530 |
| 4,829,641 A | | 5/1989 | Williams | |
| 4,891,501 A | | 1/1990 | Lipton | |
| 4,907,321 A | | 3/1990 | Williams | |
| 4,910,978 A | * | 3/1990 | Gordon et al. | ................. 62/530 |
| 4,986,076 A | | 1/1991 | Kirk et al. | |
| 5,009,828 A | | 4/1991 | McCree | |
| 5,031,418 A | * | 7/1991 | Hirayama et al. | ............. 62/530 |
| 5,036,779 A | * | 8/1991 | Capraro | ....................... 607/108 |
| 5,070,584 A | | 12/1991 | Dais et al. | |
| 5,088,487 A | * | 2/1992 | Turner | ......................... 607/108 |
| 5,140,727 A | | 8/1992 | Dais et al. | |

*Primary Examiner*—Melvin Jones

(57) ABSTRACT

Ice bag covers, articles and methods useful in the creation of a non-constrictive ice bag device that is compact and can be attached to a garment, said ice bag device comprising (a) an outer cover with extended peripheries to attach said outer cover to the inside or the outside of a garment using a plurality of safety pins; (b) a cooling medium, optionally in a liquid impermeable inner container that can fit inside the outer cover, said inner cooling container preferably being a plastic zipper bag which is sealed on three sides and having the fourth side open, the fourth side preferably having a rib and groove sealing closure; and (c) a plurality of safety pins for use to attach the ice bag device to a garment and to close the open side(s) of the outer cover; and wherein the ice bag device is optionally packaged in association with a set of instructions for use to direct the consumer how to use the product properly, to ensure that the consumer knows what benefits can be achieved, and how best to obtain these benefits, and a method of doing business in which an established entity, especially a sports organization is used to assure the user that the device and method of use are safe and effective.

20 Claims, 4 Drawing Sheets

U.S. PATENT DOCUMENTS

| | | |
|---|---|---|
| 5,148,804 A | 9/1992 | Hill et al. |
| 5,167,655 A | 12/1992 | McCoy |
| 5,484,448 A * | 1/1996 | Steele et al. ............ 607/108 |
| 5,545,197 A | 8/1996 | Bowen |
| 5,647,100 A | 7/1997 | Porchia et al. |
| 5,792,213 A | 8/1998 | Bowen |
| 5,800,491 A * | 9/1998 | Kolen et al. ............ 607/108 |
| 5,887,437 A | 3/1999 | Maxim |
| 5,967,308 A | 10/1999 | Bowen |
| 6,036,004 A | 3/2000 | Bowen |

* cited by examiner

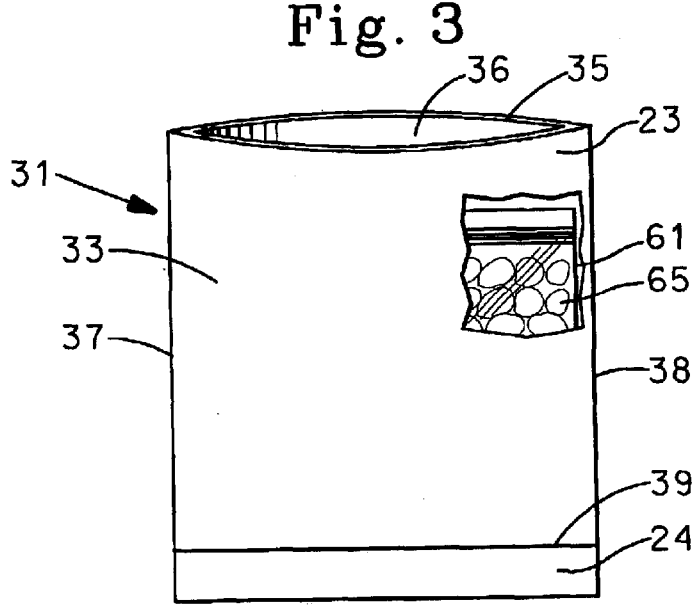
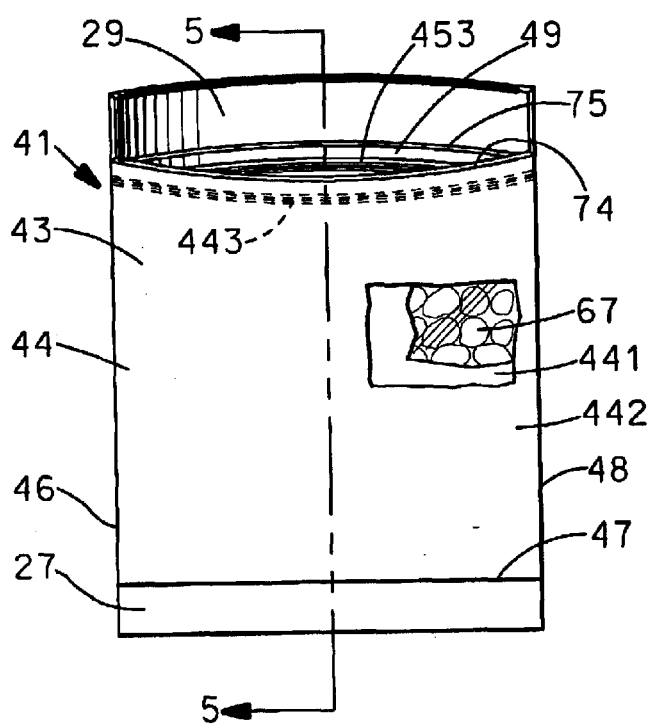
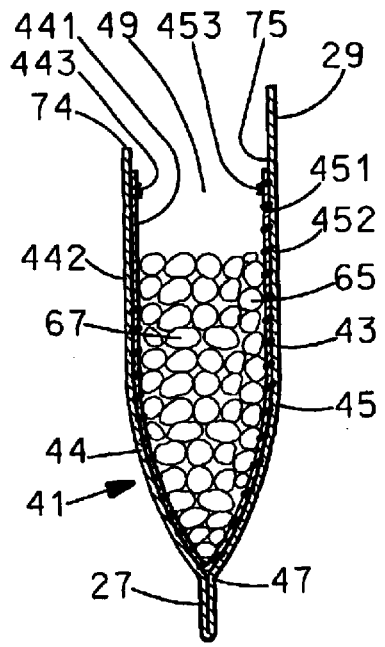

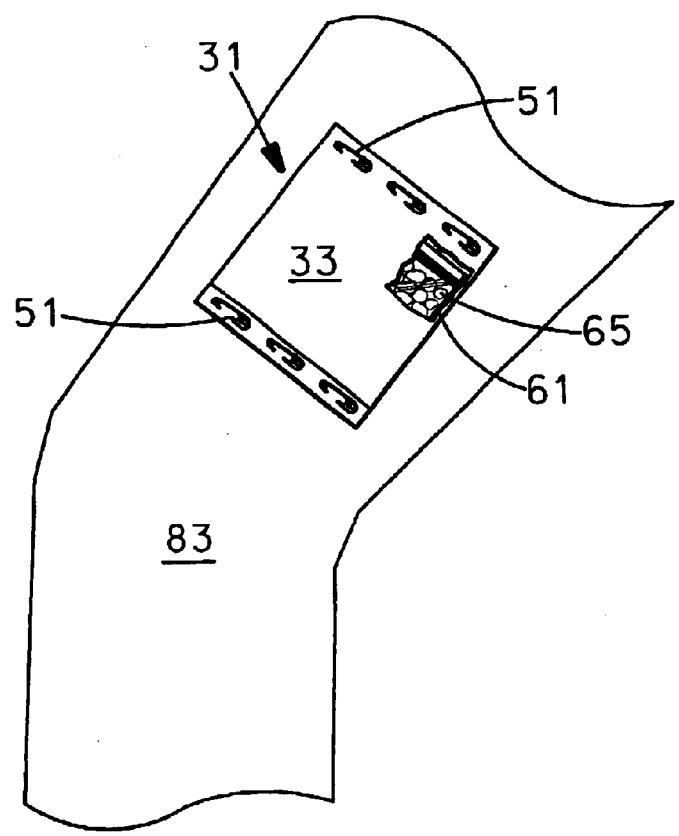
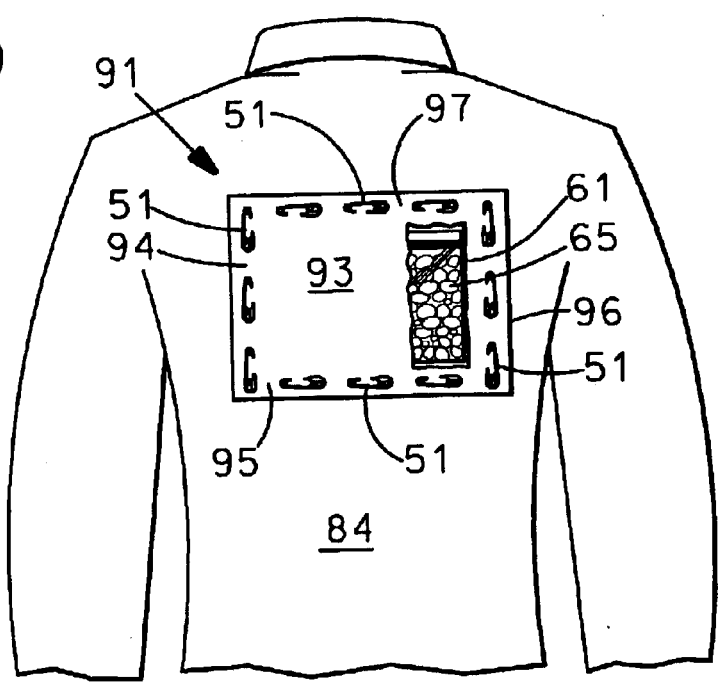

## NON-CONSTRICTIVE ICE BAG DEVICE

BACKGROUND OF THE INVENTION

1. Field of the Invention

This invention relates to the general field of medical devices and/or methods for cooling injured body parts to, e.g., alleviate pain and inflammation. In particular, it relates to an improved cover for ice bags and a method of providing an ice bag device using said cover that can be applied to an injured body part with improved comfort, convenience, and availability. Thus, it relates to a cover for ice bags that can be attached to a garment, said ice bag cover being compact, e.g., to fit in first-aid boxes to be used at home or away from home, e.g., in sporting events, such as at a soccer field or basketball court, outings in a park, picnics, and/or on trips. It also relates to an article of manufacture that provides such cover, to the method of fabricating and/or using such ice bag device using such cover; to the provision with the cover of instructions for use that aid unskilled users to provide effective emergency assistance ("first aid treatment") to injured body parts, and to methods of doing business that promote the availability of such covers, articles of manufacture, and methods, etc., to the maximum number of people who may need such first aid treatment.

2. Description of the Related Art

The desirability of using ice bags for thermal therapy is well accepted. Ice bags enable the user to apply cold to an injury such as a bruise or sprain without unacceptable mess. A common ice bag that is commercially available is the reusable type comprising a water-impermeable, commonly a rubber-lined, flexible bag having a tubular rigid neck and a removable cap. To use, the bag is filled with ice cubes or ice chips and closed with the cap, then the bag is applied to the bruised body part and held in place by hand.

Another type of cold pack that is commercially available is a refrigeratable gel cold pack which comprises a refrigerant or coolant gel material contained in a plastic housing which can be either flexible or relatively inflexible. The gel packs are stored in a freezer for chilling or cooling and are then ready for use. Also commercially available is a chemical pack which comprises two or more pouches for separately storing chemical reactants which can be mixed to produce an endothermic cooling mixture.

A common home-use ice bag can be made using a commercially available reclosable plastic sandwich or freezer bag with a zipper seal, such as a Ziploc™ plastic bag filled with ice (Ziploc is a registered trademark of Dow Chemical Company, Midland, Mich.). By "reclosable" it is meant that the bag can be open and closed numerous times.

One of the disadvantages of these ice bags is that they need to be inconveniently held by hand to maintain contact with the injured body part. To overcome this inconvenience, several types of ice bag devices comprising a holder for these ice bags have been created. These ice bag devices can be strapped around a body part, with, e.g., loop and hook mating Velcro™-type fastening straps. Since ice bag devices need to be wrapped and tied around a body part, they are constrictive and can interfere with the blood flow. Furthermore, these ice bag devices are usually of complicated design, large and bulky in size and/or expensive to produce and/or difficult to be washed for reuse.

U.S. Pat. No. 5,887,437 issued Mar. 30, 1999 to Maxim discloses a chemical cold pack that does not have fastening straps, but instead has an extended perimeter with adhesive means to attach the chemical cold pack to a skin surface. However when this self-adhesive chemical cold pack is applied to an unwashed and likely profusely sweaty skin surface of a bruised body part of an athlete who is injured in the field, the sweaty and/or soiled skin surface can make a common adhesive means less adhering. The adhering means can be made to be more strongly sticky, but in this case the removal of the device from the skin surface after use can be more uncomfortable, especially when the skin area is already bruised. This particular cold pack is not intended for reuse.

To overcome the constriction effect of the strapping, there are efforts to develop garments or other devices that can provide the cold therapy without the need to be tightly strapped and/or wrapped. U.S. Pat. No. 2,403,676 issued Jul. 9, 1946 to Modlinski discloses a jacket with a plurality of attached pockets to hold ice packs or ice bags. U.S. Pat. No. 4,891,501 issued Jan. 2, 1990 to Lipton discloses a therapeutic pad, with cooling elements, that can be hung around the neck or the head to treat the muscles of the neck, the chest, the back, and/or the jaw. U.S. Pat. No. 5,167,655 issued Dec. 1, 1992 to McCoy discloses a cold therapy panty provided with a receptacle located adjacent to the crotch area to receive a cold pack for applying cold therapy to the crotch of the wearer. U.S. Pat. No. 4,033,354 issued Jul. 5, 1977 to De Rosa discloses an ice cooling vest-like garment comprising water-filled pockets that are frozen and subsequently attached via Velcro fasteners to the inside of the garment so as to provide body cooling under heat stress conditions. Although these cold pack devices provide an improvement over the prior art, they are of complicated design, large and bulky in size and/or expensive to produce and/or difficult to be washed for reuse.

Thus, there is a need for an improved, inexpensive and readily available ice bag device that can be attachable in some manner without being held by hand, and preferably without being strapped and/or tied around a body part, because such strapping can be constrictive and can interfere with the blood flow. Preferably such ice bag device is compact, not bulky, so that preferably it can fit in a first-aid box along with other first-aid items. Preferably such ice bag device is easily manufactured and used.

BRIEF SUMMARY OF THE INVENTION

This invention relates to, alternatively: (A) a non-constrictive flexible ice bag outer cover for at least one inner "cooling bag", or inner cooling pack, hereinafter simply "pack" or "packs", containing cooling medium, preferably said outer cover having an extended periphery on at least one side to permit attaching said outer cover, when it is assembled and filled with at least one cooling pack containing cooling medium, to the inside or the outside of a garment using a plurality of safety pins, wherein "plurality" is typically from 1 to about 20 safety pins, such that said cooling medium is in close contact with an injured body part of an individual, without the need for a strapping and/or wrapping means, wherein said outer cover typically comprises a piece of flexible substrate, such as a piece of fabric, more preferably said outer cover being a sack structure (or pouch structure) with one or more open ends (or sides) and having two or more extended peripheries (or extended sides, or extended edges) that have a width of at least about 0.5 centimeter, more preferably of at least about 1 centimeter, and wherein said cooling medium is contained in either a resealable or sealed, typically flexible, typically plastic, liquid impermeable inner container to form an inner cooling pack, wherein said cooling medium is preferably either ice, ice and water combination, refrigeratable cooling gel, or endothermic chemical cooling system, wherein said inner cooling pack can be inserted through said open end(s) and/or side(s) of said outer cover, and wherein said open end(s) and/or side(s) are capable of being sealed to retain the said inner cooling pack using the said safety pins or the outer cover is sealable or sealed and comprises a liquid impermeable layer and the cooling media is inside the outer cover; (B) a method for first aid treatment of injuries by using safety pins to attach the outer cover (A) which holds an inner, typically plastic, typically flexible, fluid impermeable container containing a cooling medium to a garment to apply said cooling medium to an injured body part when the garment is worn; and preferably, a method of creating a non-constrictive ice bag device using said outer cover by filling an inner plastic zipper bag container that is sealable by interlocking rib and groove sealing closure, with ice or an ice and water combination, placing the filled inner plastic zipper bag container inside said outer cover, using a plurality of safety pins to attach the assembled ice bag device to the inside or the outside of a garment, such that said ice bag device is in close contact with an injured body part of an individual when the garment is worn, and optionally, but very preferably, using said safety pins to seal or close said outer cover; (C) the completed non-constrictive ice bag device comprising said outer cover (A) and at least one said inner flexible liquid impermeable inner cooling container filled with cooling medium prepared by the said method (B), and a plurality of safety pins; (D) the combination of either said non-constrictive outer cover (A), or the non-constrictive ice bag device (C), in association with instructions for the said method (B), to ensure that the method can be practiced efficiently, quickly, and effectively, especially by untrained personnel, so as to maximize the effect of the cooling treatment on an injury, especially with respect to the speed with which the cooling medium is applied to the injured body part; (E) an article of manufacture comprising a non-constrictive flexible outer cover (A), optionally, one or more resealable or sealed liquid impermeable containers as disclosed in (B), optionally, a plurality of safety pins, optionally, a sealed plastic bag wrapper to keep the outer cover and the optional elements in a hygienic, non-contaminated condition in storage and/or to prevent accidental loss of one or more of the elements, and optionally packaged in association with instructions for use as disclosed in (D), said instructions for use comprising an instruction to direct the consumer to attach the assembled ice bag device to the inside or the outside of a garment; and (F) the method of doing business in which the cover disclosed in (A), the ice bag device disclosed in (C), the instructions for following the method disclosed in (D), and/or the article disclosed in (E) are distributed with the approval of one or more organizations so as to maximize the availability of the cover, the ice bag device and/or method where they are needed and/or to provide assurance that the method, device, instructions, etc. are effective and safe and preferably in association with an indicia of such organization.

The present invention also relates to a method of using safety pins to attach an ice bag device to a garment such that said ice bag device is in close contact with an injured body part of an individual when the garment is worn, and/or to close the opening of the outer cover of said ice bag device, wherein said ice bag device comprises a flexible outer cover containing an inner cooling container filled with a cooling medium and the said safety pins are used to attach the said outer cover to the said garment.

BRIEF DESCRIPTION OF THE DRAWINGS

FIG. 3 is a perspective view of an alternative embodiment of the ice bag device of he present invention, in an open configuration, showing a flexible outer cover with a sack structure with one open end, holding an inner reclosable zipper bag containing ice chips, said outer cover being partly cut away to show said inner zipper bag;

FIG. 4 is a perspective view of an alternative embodiment of the ice bag device of the present invention, in an open configuration, showing a liquid impermeable outer cover with a unitary structure to contain ice, wherein the outer cover layer and the inner container layer are laminated together, said cover having a sack structure with three closed sides and one open side, wherein the open side is sealable by a leak-proof zipper closure to retain the ice, and with two peripheries that are extended from the open side and the closed side opposite to the open side, said outer cover being partly cut away to show the contained ice;

FIG. 5 is a side, cross-sectional view of the ice bag device of FIG. 4 comprising the laminated outer cover containing ice taken along the line 5—5;

FIG. 8 is a view of the ice bag device of FIG. 3 being attached to the outside of a leg of a pair of pants by a plurality of safety pins, with the outer cover being partly cut away to show the ice-filled inner zipper bag; and FIG. 9 is a view of an alternative embodiment of the ice bag device of the present invention comprising a flexible outer cover comprising a rectangular piece of flexible substrate, holding an inner reclosable zipper bag containing ice chips, with the outer cover being partly cut away to show the ice-filled inner zipper bag, and with said ice bag device being attached to the outside of the back of a shirt by a plurality of safety pins.

DETAILED DESCRIPTION OF THE INVENTION

Figure 1:
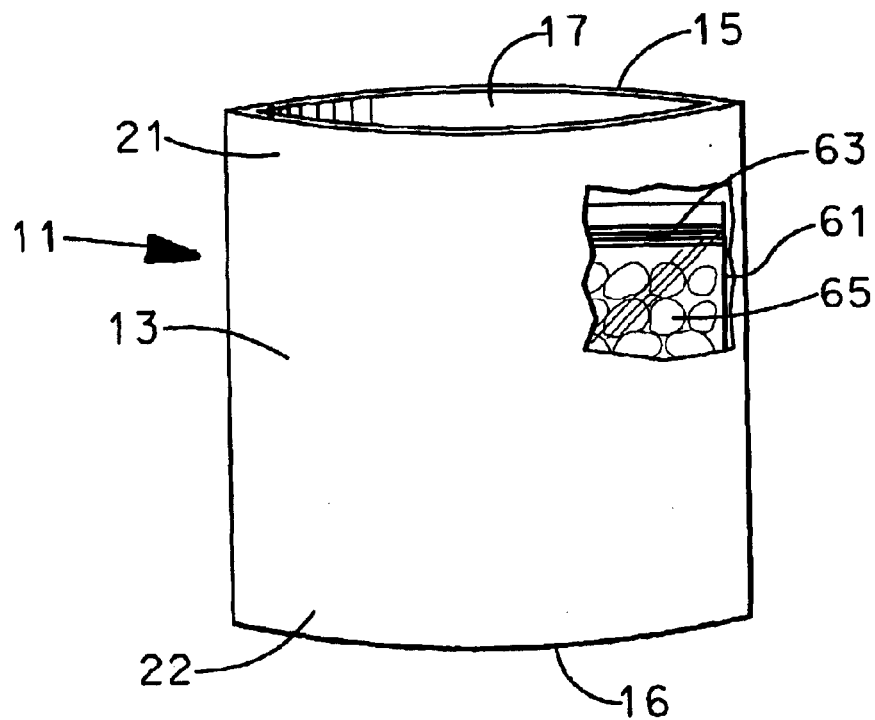
FIG. 1 is a perspective view of an ice bag device of the present invention, in an open configuration, comprising a flexible outer cover with a tubular structure with two pen ends, holding an inner reclosable zipper bag containing ice chips, said outer cover being partly cut away to show said ice-filled inner zipper bag.

Youth contact sport activities such as soccer, football and basketball are more and more popular. Unavoidably, some occasional bruises and injuries such as sprains accompany these activities. Thus, there is a need for an inexpensive and readily available ice bag device for such events. Such ice bag devices need to be attachable in some manner without being held by hand, because while the injured player would likely prefer to stay to watch until the end of the game, he or she does not want to hold the ice bag with his or her hand for the duration of the game. Applying the ice bag device by hand not only is inconvenient, but it also can restrict the mobility if the injury is, e.g., in a lower part of the body such as in the leg or foot, and it can be awkward if the injury is, e.g., in a hard to reach body part such as on the back. Furthermore, such ice bag preferably should not be strapped and/or tied around a body part, because such strapping can be constrictive and can interfere with the blood flow. It is also preferred that the cold should not reduce the skin temperature excessively since that can cause damage, e.g., frostbite. Such ice bag is preferably easily washable or optionally disposable, because it is most likely applied to an unwashed and likely sweaty body part. Injury that needs an ice bag treatment also can happen in other types of outdoor activity such as picnicking, hiking and other outings, and/or on trips. Such ice bag device needs to be compact, not bulky, so that preferably it can fit in a first-aid box along with other first-aid items. Preferably such ice bag device is easily manufactured and used.

In one aspect of this invention there is provided a flexible outer cover for a non-constrictive ice bag device that is attached to the inside or the outside of a garment, using a plurality of safety pins, at a location on the garment that is in close contact with the injured area of the body, when the garment is worn, without the need for a strapping and/or wrapping means. "Garment", as used herein, means a piece of clothing that is worn to cover a part of the body, such as shirt, jacket, coat, pants, trousers, shorts, underwear, hat, sock, scarf, glove, and the like.

Thus, the present invention relates to a flexible outer cover for an ice bag device, said cover being either a piece of flexible substrate or a sack structure with one or more open sides, having one or more extended peripheries (edges), preferably substantially free of adhesive, for use to attach the outer cover to the inside or the outside of a garment by the use of a plurality of safety pins, wherein each extended periphery has a width of at least about 1 centimeter, and wherein said cover has dimensions to form one or more compartments suitable for containing one or more cooling packs which can comprise a generally liquid impermeable container capable of containing a cooling medium or which can contain cooling media when the cover is relatively liquid impermeable and sealable.

The outer cover can have any suitable shape such as rectangular, square, round, oval, and the like. Preferably the flexible outer cover has a generally rectangular or square configuration when flattened to facilitate storage and to more efficiently contain typical cooling bags. Typically the outer cover has two faces or sides that join together at the edges to form a sac or pouch structure having one or two open ends and three or two closed edges. The flexible outer cover is preferably a unitary structure, typically either a piece of flexible substrate, such as a piece of fabric, or said outer cover is a sack structure (or pouch structure) having one or more open sides (or ends), e.g., a sack structure (or pouch structure) with one open side or a generally tubular structure with two open sides, and having two or more extended peripheries (or extended sides or extended edges) for use to attach the outer cover to the garment, using the safety pins. Thus, the outer cover can be a single piece of substrate that, when attached to a garment surface using the safety pins, forms a compartment to enclose an inner cooling pack comprising an inner container containing a cooling medium. More preferably, the outer cover is either a sack structure with one open end or a tubular structure with two open ends wherein the inner cooling pack is inserted.

Figure 2:
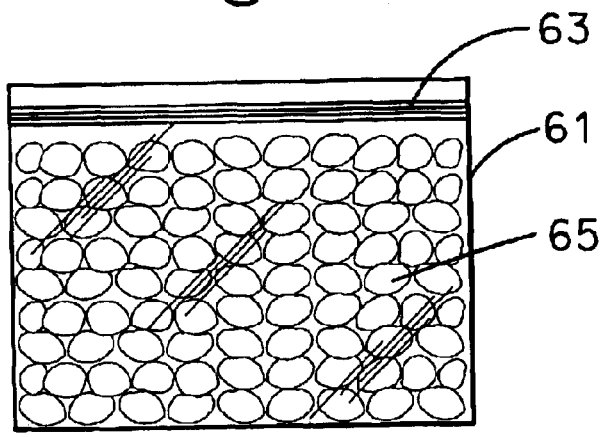
FIG. 2 is a plan view of the isolated zipper bag filled with ice chips of the ice bag device of FIG. 1.

The periphery of the outer cover can be extended on all four sides for use to attach said outer cover to a garment using the safety pins, such as in the case of a single substrate, or can be extended on only two or three sides, preferably two opposite sides, preferably the sides that have the open ends. For a closed side, the width of its extended periphery is from the sealed line to the edge of the side, as is depicted in FIG. 2. For an open side, the width of its extended periphery is approximately defined by the gap between the edge of the outer cover and the edge of the inner cooling pack, as is depicted in FIG. 1 and FIG. 2. In another embodiment, the outer cover has two peripheries that are extended from the two opposite closed sides that are used in the attachment of the outer cover to a garment, while the open end that is preferably located on the top side remains open for an easy insertion and/or exchange of the inner cooling pack(s). The periphery extension typically has a width of from about 0.5 cm to about 10 cm, preferably from about 1 cm to about 5 cm, more preferably from about 1.5 cm to about 3 cm.

The outer cover is made at least partly of a relatively flexible substrate. The substrate is typically a fabric, normally woven and/or non-woven and/or knitted, but can also be a resilient foam sheet. The outer cover can be made of material such as, but not limited to, woven, knitted, crocheted, or non-woven fabric of natural and/or synthetic fibers such as cotton, polyester, nylon, acrylic, rayon, and the like, felt, velvet, flocked material, heat-bonded plastic fiber material, such as, melt-blown, spun-bonded polyethylene or polypropylene, carded thermo-bonded polypropylene and rayon blend, solvent-laid thermally bonded polypropylene (e.g., Tyvek™, by Dupont), resilient open-ell or close-cell plastic foam sheet, porous and nonporous plastic film and/or rubber, paper, laminated materials such as laminate of rubber and non-woven layers, and the like. It is also permissible to have the outer cover be water impermeable and sealable to eliminate the need for the inner cooling pack. However, the different requirements for the outer cover and the inner pack make it highly preferable to provide both the outer cover and the inner pack. It is easier to wash the outer cover when it is fabric and it is easier to fabricate when there is no need to have it water impermeable.

The edges of the outer cover can be sealed by sewing, gluing, heat sealing, or the like, or can be integral, e.g., when formed from tubular material that requires no sealing on the side edges. The preferred material makes the outer cover of the ice bag device flexible, conformable, and optionally stretchable, at least on the side that is in contact with the body. The material that contacts the body also preferably slows the cooling of the body part to avoid damage by overcooling, e.g., frostbite. The material should allow heat to flow from the injured body part. Preferably, the material does not allow heat to flow through it at a rate that will result in frostbite. The desired effect is cooling without freezing and the cooling is preferably at a rate that produces no more pain than can be withstood by the user and which does not cause damage to the treated area.

The outer cover can most conveniently have one compartment designed to have dimensions suitable to hold one inner cooling pack comprising an at least relatively liquid impermeable inner container containing a cooling medium. The inner cooling pack can be inserted into the compartment through the open side of the outer cover, and said open side is preferably capable of being sealed using the safety pins. The inner cooling pack is preferably composed of a resealable or permanently sealed plastic liquid impermeable inner container to contain a cooling medium, wherein said cooling medium is preferably either ice, ice and water combination, water, refrigeratable cooling gel, or endothermic chemical cooling system. Ice, and ice and water mixtures are preferably contained in a resealable or reclosable plastic bag container, such as a reclosable zipper bag, which is conveniently either a commercially available reclosable zipper bag such as a sandwich or freezer zipper bag, as described hereinafter, or a specially made zipper bag of any suitable size and thickness. The use of a reclosable bag allows one to replace the cooling medium when it is no longer cool. Refrigeratable cooling gel and/or endothermic chemical cooling system are preferably contained in a permanently sealed plastic container. The permanently sealed plastic container can also contain liquid water to be placed in, e.g., a conventional freezer to form ice for use in the method and/or article of the present invention. In this embodiment, provision should be made for the expansion of the water when it freezes, either by having sufficient void space or by making the container expansible.

The outer cover can also be divided into two or more compartments to hold two or more inner cooling packs. The preferred multi-compartment outer cover has two or three compartments, more preferably two compartments, especially for compact size inner cooling packs. An ice bag device of the present invention having multiple compartments has the advantage of distributing solid cooling media such as ice chips or ice cubes more evenly on the skin surface, and better preventing the ice from accumulating into one area, thus providing more even cooling and/or comfort. The outer cover is conveniently separated into two or more compartments, preferably of approximately equal size, by sewn lines, glue lines or staple lines that are stitched or otherwise added into the outer cover.

Preferably the compartment(s) of a multi-compartment outer cover have dimensions that can accommodate/fit the reclosable inner cooling packs comprising commercially available plastic zipper containers of the quart size or sandwich size as described hereinafter. A preferred multi-compartment outer cover has compartments that can hold inner cooling packs comprising plastic zipper containers which are commercially available reclosable snack bags, as described hereinafter.

Another aspect of this invention relates to an ice bag device that can be attached to a garment, said ice bag device comprising:

(a) an outer cover as described hereinabove;

(b) one or more preferably plastic, preferably reclosable, liquid impermeable inner containers, preferably rectangular or square in shape, containing cooling media such as ice cubes, ice chips, crushed ice, or ice and water mixture, to form inner cooling packs, or ice bags, wherein said inner cooling packs can fit inside the enclosure of the outer cover, and wherein each said inner cooling container is closed, e.g., sealed, on three sides and has the fourth side open, preferably having a reclosable closure, more preferably a rib and groove sealing closure (zipper closure); and (c) a plurality of safety pins, at least one, preferably at least about two, more preferably at least about four, and less than about 20, preferably less than about 16, and more preferably less than about 12 safety pins, for use to attach the outer cover to the inside or the outside of a garment and/or to close any open side(s) of the outer cover;

and wherein the optional ice-filled inner cooling pack(s) of (b) can optionally be replaced by chilled or frozen gel pack(s) and/or chemical cold pack(s), when said pack(s) are available.

In particular, this invention relates to an assemblage of elements, comprising an outer cover as disclosed herein, one or more zipper bags, and a plurality of safety pins, that can be used to create an ice bag device, that is compact, e.g., can fit in a first-aid box along with other first-aid items, to be used at home or away from home, e.g., in sporting events, such as at a soccer field or basketball court, in other outings such as hiking or picnic, and/or on trips. Such elements are preferably easily manufactured and/or inexpensive.

A preferred inner container is constructed of a liquid impermeable, e.g., waterproof, synthetic "plastic" material such as a polyethylene film. Such inner container preferably is a reclosable zipper bag which is closed (e.g., sealed) on three sides and has the fourth side that is open but that preferably has a reclosable closure, preferably an interlocking rib and groove, or male and female sealing closure, as described, e.g., in U.S. Pat. No. 3,338,284 issued Aug. 29, 1967 to Ausnit; U.S. Pat. No. 4,263,079 issued Apr. 21, 1981 to Sutrina et al.; U.S. Pat. No. 4,363,345 issued Dec. 14, 1982 to Scheibner; U.S. Pat. No. 4,829,641 issued May 16, 1989 and U.S. Pat. No. 4,907,321 issued Mar. 13, 1990, both to Williams; U.S. Pat. No. 5,009,828 issued Apr. 23, 1991 to McCree; U.S. Pat. No. 5,070,584 issued Dec. 10, 1991 to Dais et al.; U.S. Pat. No. 5,140,727 issued Aug. 25, 1992 to Dais et al.; U.S. Pat. No. 5,647,100 issued Jul. 15, 1997 to Porchia et al.; and the references cited therein.

Preferred inner containers are rectangular or square in shape. Each inner container can be defined by two sets of dimensions, namely, the outer dimension that includes the sealing closure line or part, and the inner dimension that counts only the storage area, without the sealing closure part. Each dimension is typically defined by two sides, the first side is a lateral or opening side and the second side is a vertical closed side. In use, the inner container(s) can be filled with, e.g., ice cubes, ice chips, crushed ice, or ice and water mixture, then the resealable closure is firmly pressed along the sealing closure line in order to hermetically seal the resulting inner cooling pack(s) or ice bag(s). Preferably the sealing closure part is folded back onto one side of the inner bag before the inner bag is placed in a compartment of the outer cover, in order to maximize the cold contact surface and/or to better maintain the seal against any accidental opening due to pressure applied on the side of the ice bag device.

Preferred reclosable inner containers for use in the ice bag device of the present invention are the commercially available household reclosable plastic zipper bags for use as food containers or freezer storage bags, and sold, e.g., under the brand names Ziploc® or Glad®, or store name, e.g., Kroger®, and the like. The preferred commercially available household zipper bags for use in an outer cover that has one compartment are the quart size bags (typically having an outer dimension of from about 17 cm×21.5 cm to about 18.5 cm×23 cm, and an inner dimension of from about 17 cm×19.5 cm to about 18.5 cm×21 cm) or the sandwich bags (typically having an outer dimension of from about 16 cm×18.5 cm to about 17 cm×18.5 cm, and an inner dimension of from about 16 cm×14 cm to about 17.5 cm×16 cm). The preferred commercially available household zipper bags for use in an outer cover that has more than one compartment are the sandwich zipper bags (typically having an outer dimension of from about 16 cm×18.5 cm to about 17 cm×18.5 cm, and an inner dimension of from about 16 cm×14 cm to about 17.5 cm×16 cm) or the snack size zipper bags (typically having an outer dimension of from about 16 cm×9 cm to about 17 cm×11.5 cm, and an inner dimension of from about 16 cm×7.5 cm to about 17 cm×9 cm). Industrial zipper bags of many sizes are also available, e.g., from Lab Safety Supply, Inc., Janesville, Wis.

The inner zipper containers can be made of plastic film, preferably transparent plastic film. One common material used in the household and industrial zipper bags is polyethylene. The zipper bags that are useful as inner containers of the present invention typically have a film thickness of from about 0.01 mm to about 0.25 mm, preferably from about 0.02 mm to about 0.15 mm, more preferably from about 0.02 mm to about 0.1 mm, and even more preferably from about 0.03 mm to about 0.08 mm.

The ice in the inner cooling pack can be ice chips, but is preferably in the form of small pieces, e.g., pieces having a maximum dimension of at least about 1 cm, preferably at least about 2 cm, more preferably at least about 3 cm and less than about 10 cm, preferably less than about 8 cm, more preferably less than about 7 cm. Although the ice will not be in contact with the skin, it is highly preferred that the ice be hygienic and potable.

The outer cover can optionally be used to hold and apply other cold media in place of the ice-filled inner cooling pack. Non-limiting examples of such cold media include a pre-cooled gel pack, or a chemical cold pack. A cold gel pack is a refrigeratable gel cold pack that comprises a refrigerant or coolant gel material contained in a permanently sealed plastic housing which can be either flexible or relatively inflexible. The gel packs are stored in, e.g., a conventional household freezer for chilling or cooling and are then ready for use. Non-limiting examples of cold gel packs and/or coolant compositions are given in U. S. Pat. No. 3,780,537 issued Dec. 25, 1973 and U.S. Pat. No. 3,885,403 issued May 27, 1975, both to Spencer, and U.S. Pat. No. 5,148,804 issued Sep. 22, 1992 to Hill et al. Many commercially available gel packs, such as the Nexcare™ First Aid Reusable Cold Pack produced by 3M Health Care, St. Paul, Minn., Ace® Brand Cold Compress Reusable and Ace Brand Hot & Cold Compress Reusable distributed by BD Consumer Healthcare, Franklin Lakes, N.J., are elongated in dimension with sizes of from about 23 cm×9.5 cm to about 27 cm×12.5 cm. When they are stored in a household freezer, they are chilled but not frozen. They can be folded in two in order to be placed in a compact outer cover with one compartment of the present invention that is designed to accommodate one sandwich zipper bag. Preferably they can be used in an elongated outer cover that is specifically designed to accommodate the elongated gel packs. The permanently sealed plastic container can also contain liquid water to be placed in, e.g., a freezer to form ice for use in the method and/or article of the present invention. The frozen ice contained in such permanently sealed plastic container adopts the shape of the container and has the dimension of such container, including dimension larger than about 10 cm.

A chemical cold pack typically comprises an endothermic chemical system comprising different chemicals which, when mixed together, undergo an endothermic reaction to reduce the temperature of the cold pack. Typically, the different chemicals are contained in separate compartments to prevent a premature reaction. The chemical cold pack is "activated" when the compartments are, e.g., connected by a certain means so that the chemicals are mixed to produce the endothermic reaction. An example of such endothermic chemical system is dry ammonium nitrate and water. Other non-limiting examples of endothermic chemical systems and/or chemical cold packs are given in U.S. Pat. No. 2,882,692 issued Apr. 21, 1959, U.S. Pat. No. 2,898,744 issued Aug. 11, 1959, U.S. Pat. No. 3,058,313 issued Oct. 16, 1962, all to Robbins; U.S. Pat. No. 2,925,719 issued Feb. 23, 1960, to Robbins et al.; U.S. Pat. No. 3,643,665 issued Feb. 22, 1972 to Caillouette; U.S. Pat. No. 3,893,834 issued July 8, 1975 to Armstrong; U.S. Pat. No. 4,986,076 issued Jan. 22, 1991 to Kirk et al.; and U.S. Pat. No. 5,545,197 issued Aug. 13, 1996, U.S. Pat. No. 5,792,213 issued Aug. 11, 1998, U.S. Pat. No. 5,967,308 issued Oct. 19, 1999, and U.S. Pat. No. 6,036,004 issued Mar. 14, 2000, all to Bowen.

The safety pins are used to attach the outer cover that holds the inner cooling pack containing a cooling medium, to the inside or the outside of a garment such that said cooling medium is in close contact with an injured body part of a user without the need for a strapping means, and/or to close the open end(s) of the outer cover. The safety pins can serve as a closure for the opening end(s) of the outer cover, in addition to being used for attaching the ice bag device to a garment. Thus the need for a separate closing mechanism for the opening of the ice bag outer covers, mostly with the use of the expensive Velcro strips, as described in other ice bags of the art, is rendered unnecessary.

Any type of safety pin can be used in the ice bag device of the present invention to attach the outer cover to a garment. The most common and a preferred type of safety pin for use in the present invention is the Clinton type safety pin that is illustrated, e.g., in FIG. 4 of U.S. Pat. No. 1,623,532 issued Apr. 5, 1927 to Dudas, said patent being incorporated, herein by reference. This type of safety pin is made of a piece of wire and comprises a bridge-bar which is bent at one end about one and one half turn to form a spring-loop which terminates with a pointed wire extension forming a pin-bar. At the opposite end of the spring-loop the bridge-bar is terminated with an upward bend upon which a substantially U-shape safety pin cap (a protective sheath) is clamped. The upper part of this clamp is adapted to receive the pointed end of the pin-bar when the safety pin is closed. This type of safety pin is flat in shape and is very suitable and comfortable to wear with the ice bag cover of the present invention.

The most common safety pins are of the straight type wherein the bridge-bar and the pin-bar are substantially straight and parallel with each other. Curved or bent safety pins are also available. In a common type of curved safety pin, both the bridge-bar and the pin-bar are curved or bent in the same direction, preferably with the pin-bar being the protruding member, to facilitate the piercing of the extended periphery of the outer cover and the garment fabric. Both straight and curved safety pins are commercially available, e.g., from Prym-Dritz Corporation, Spartanburg, S.C.

Safety pins that are suitable for use in the present invention typically have an overall length of from about ¼ in. (about 18 mm) to about 3 in. (about 75 mm), preferably from about 1 in. (about 25 mm) to about 2½ in. (about 64 mm), more preferably from about 1¼ in. (about 32 mm) to about 2 in. (about 51 mm).

In an alternative embodiment, this invention relates to a flexible, liquid impermeable outer cover with a unitary structure to contain ice, as described herein above, but wherein the outer cover layer and the inner container layer are laminated together, said cover preferably having a sack structure with three closed sides and one open side wherein the open side is sealable by a leak-proof zipper closure to retain the ice, and wherein at least one side, preferably two or more sides, more preferably the open side and the closed side opposite to the open side have extended peripheries for use to attach the outer cover to the inside or the outside of a garment by the use of a plurality of safety pins, wherein each extended periphery has a width of at least about 1 centimeter. The wall of the cover is preferably made of laminated materials such as laminates of plastic and woven or non-woven fabric layers, with the plastic layer providing the liquid impermeability and the construction of the zipper closure and the fabric layer providing a degree of insulation to slow the cooling of the treated body part, to avoid damage by overcooling, e.g., frostbite. Such unitary structures are more difficult to manufacture.

The present invention also relates to a method for first aid treatment of injuries by using safety pins to attach an ice bag device comprising an outer cover holding a cooling pack, such as an ice bag or cooling gel pack to a garment, and to thereby apply said cooling pack to an injured body part when the garment is worn. The present invention further relates to a method of using safety pins to close the opening of the outer cover of said ice bag device. This method is of great value, since in general it permits one to carry/store only the described outer cover and the safety pins, and optionally a zipper bag, as separate items, yet permitting the fabrication and use of a non-constrictive ice bag device readily and immediately when it is needed. The present invention also includes the method for first aid treatment of injuries by using safety pins to attach a commercially available outer cover containing a commercially available cooling pack to a garment, to apply said cooling pack to an injured body part when the garment is worn.

The present invention also relates to an article of manufacture comprising one or more outer covers as described hereinabove, and optionally at least one other element which is: one or more empty preferably reclosable liquid-impermeable plastic containers, or sealed, liquid impermeable, plastic containers containing a cooling medium such as water, refrigeratable cooling gel, or endothermic chemical system, preferably one or more empty reclosable zipper containers, to contain a cooling medium, that can fit inside the enclosure of the outer cover; a plurality of safety pins; and/or a sealed plastic wrapper to keep the outer cover(s), the optional inner container(s), and the optional safety pins in a hygienic, non-contaminated condition in storage and/or to prevent accidental loss of one or more of the elements, wherein the plastic wrapper can be transparent or opaque, and can be white or colored; and/or said article is optionally but preferably packaged in association with a set of instructions for use to direct the consumer to use the product properly, to ensure that the consumer knows what benefits can be achieved, and how best to obtain these benefits. The outer cover is preferably transparent or marked with the contents so that the article can be readily identified in an emergency.

The present invention also relates to the association of a set of instructions for use with the outer cover, the ice bag device, the method, or the article of manufacture described hereinabove to ensure that the method can be practiced and the cover and/or the article be used efficiently, quickly, and effectively so as to maximize the effect of the cooling treatment on an injury. The set of instructions provides the information on how to use the outer cover, the safety pins, the inner containers, and cooling media such as ice, as well as the cooling gel or the chemical cooling pack, to create a convenient non-constrictive ice bag device that provides immediate cooling to an injury.

The set of instructions of the present invention preferably includes one or more of the following instructions: to direct the consumer to place the outer cover on a location on a garment such that the contained cooling medium will be in close contact with the injured area of the body when the garment is worn, with the outer cover placed either to the inside of the garment if there is room inside the garment to fit the complete ice bag device and/or if the garment is composed of a thick layer, such as a jacket, or to place the outer cover to the outside of the garment if the garment is made of thin material that allows good transmission of cold to the injured body part, and/or if there is not enough room inside the garment, such as a pair of tight pants or a sock, then to attach the outer cover to the garment using the safety pins, leaving one or more sides of the outer cover open to insert one or more inner cooling packs comprising containers containing a cooling medium.

The set of instructions preferably also includes instructions to direct the consumer to fill the inner container(s) with cooling media such as ice cubes, ice chips or crushed ice, then to seal the filled inner container(s), then, optionally, but preferably, to fold the sealing closure back against one side of the inner container, then to place the filled inner ice bag(s) in the compartment(s) of the outer cover, and then to simultaneously close the remaining open side of the outer cover and to attach said open side to the garment using safety pins.

The set of instructions can also include an instruction to direct the consumer to pre-cool one or more gel packs, or to activate one or more chemical cool packs, for use as the inner cooling packs.

The set of instruction preferably includes an instruction to direct the consumer to close the remaining open side(s) of the outer cover and attach the extended peripheries of said open side(s) of the outer cover to the garment using the same safety pins, by carefully piercing said peripheries with the safety pins so as to avoid puncturing the inner cooling container.

The set of instructions preferably includes an instruction to direct the user to wear the garment so as to apply the resulting attached ice bag device over the injured body part where cooling can occur.

The set of instructions can include an instruction to direct the consumer to a source of ice or cold fluid, preferably including a home refrigerator, ice boxes or coolers for beverages at a sport game, and/or a fast food restaurant and/or hotel or motel when one is on a trip. There is usually some ice or cold water or other cold fluid available at sporting events.

The set of instructions can include an instruction to direct the consumer to optionally use already cooled gel pack(s) or chemical cooling pack(s) in the place of the ice-filled inner cooling pack(s).

The set of instructions can also include an instruction to direct the consumer to keep the article of the present invention in their first-aid kit. The set of instructions can include an instruction disclosing the non-constrictive nature and/or benefit of the ice bag device of the present invention as compared to other ice bag devices that have strapping. The instructions can also contain a suggestion to pre-cool the injured body part by direct application of the cooling medium, cool pack, etc. to the skin followed by the application to a garment for an effective, longer term follow up treatment. The set of instructions preferably comprises one or more of the hereinabove instructions.

The set of instructions can be printed, e.g., on one or more of: the package, the wrapper, an accompanying instruction flyer or booklet, and/or communicated via print circulars, etc., to members of sport and/or outdoor organizations, and the like.

The instructions can be in one or more languages. The instructions can be in words, or illustrative images and/or icons preferably in combination with words. It is preferable to have the instructions contain pictorial representations of the steps in preparing and using the ice bag device to supplement, or replace the written instructions when the user is not familiar with the language(s) of the instructions.

This invention further relates to an outer cover, an ice bag device and/or an article of manufacture comprising said outer cover and other elements of the ice bag device of the present invention, wherein one or more of the outer cover, the inner container(s) or bag(s), the wrapper, the package, and/or the set of instructions carry indicia showing, e.g., a logo, emblem, symbol, motif, sign, figure, mark, icon, pictogram, insignia, design, image, description, and/or advertisement for, e.g., a sport league, sport franchise, sport sponsor, non-profit or governmental organization, and/or for-profit commercial or industrial organization. The use of such indicia provides a measure of assurance to the user that the device is useful and not harmful, especially when the instructions are followed.

The above use of indicia can be used as part of the method of doing business in which the use of the outer cover, the article, etc., are promoted by using one or more existing associations, businesses, etc., to make, distribute, or recommend the ice bag article, the outer cover, and/or the method, to provide assurance to the intended user that the device is acceptable for the intended result. Since the primary benefit of the invention is to obtain fast treatment of trauma to diminish the damage to the individual, it follows that the user will normally not be a medical professional, and often will not have even basic first aid skills. It is important that these individuals know that the ice bag device is safe and effective and that the instructions are safe when followed, and that the individuals have access to basic instructions for use.

This invention relates to the method of doing business wherein the outer cover, other elements of the ice bag device and/or the article of manufacture comprising said outer cover and other elements of the ice bag device of the present invention, are distributed with the approval of one or more entities having an association with individuals that are likely to be injured and need an ice bag device on an urgent basis, such as an amateur or professional athletic association and/or optionally, attaching the indicia of at least one of said entities to said article and/or associating said indicia with said article.

Specific embodiments are described hereinafter with reference to the drawings.

Figure 6:
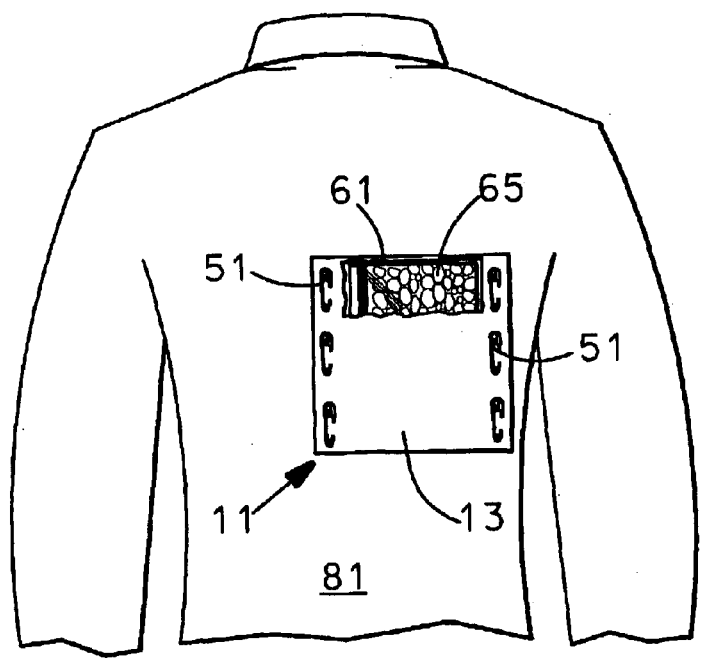
FIG. 6 is a view of the ice bag device of FIG. 1 being attached to the outside of the back of a shirt by a plurality of safety pins, with the outer cover being partly cut away to show the ice-filled inner zipper bag.

FIG. 1 shows a perspective view of an ice bag device of the present invention, in an open configuration, designated as 11. The ice bag device 11 includes a flexible outer cover 13. The outer cover 13 is of a tubular structure having two open ends (or sides) 15 and 16, and a cover interior 17. FIG. 1 also shows outer cover 13 partly cut away to show a water-impermeable inner plastic zipper container 61 with a reclosable, interlocking rib and groove sealing closure 63, and filled with ice chips 65. The two open ends 15 and 16 have extended peripheries 21 and 22 for use as a place for the safety pins to attach the ice bag device 11 to a garment. The width of the peripheries 21 and 22 is at least about 1 cm, preferably at least about 1.5 cm, so that the user has enough room to pierce the extended peripheries of the outer cover with the safety pins without a risk of puncturing the inner zipper container. The ice bag device 11 containing the inner zipper container 61 can be attached, e.g., to the garment 81 using a plurality of safety pins 51, as is shown in FIG. 6. The safety pins 51 also provide the means to close the two open ends 15 and 16 of the outer cover 13.

FIG. 2 is a plan view of the isolated zipper bag container 61 of the ice bag device 11 of FIG. 1, with a reclosable, interlocking rib and groove sealing closure 63, filled with ice chips 65, that is to be placed in the cover interior 17 of the outer cover 13 of FIG. 1.

Figure 7:
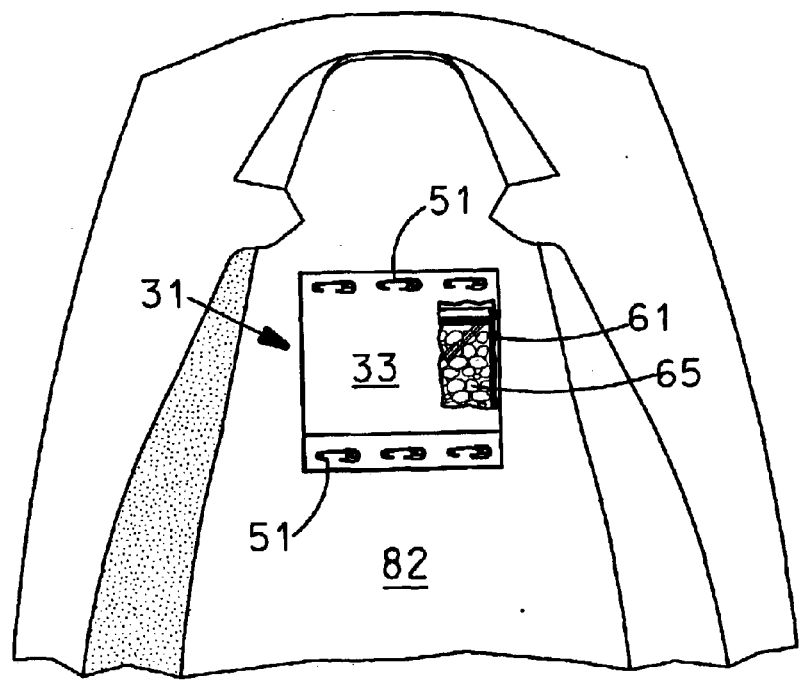
FIG. 7 is a view of the ice bag device of FIG. 3 being attached to the inside of a jacket by a plurality of safety pins, with the outer cover being partly cut away to show the ice-filled inner zipper bag.

FIG. 3 shows a perspective view of an alternative embodiment of the ice bag device of the present invention, in an open configuration, designated as 31. The ice bag device 31 includes a flexible outer cover 33. The outer cover 33 is of a sack structure having one open end (or side) 35, two opposing closed sides 37, 38 and a closed bottom side 39, and a cover interior 36. The open end 35 has an extended periphery 23 and the closed bottom side 39 has an extended periphery (or extended edge) 24 for use as a place for the safety pins to attach the ice bag device to a garment. The width of the extended peripheries 23 and 24 are at least about 1 cm, preferably at least about 1.5 cm. FIG. 3 also shows the outer cover 33 partly cut away to show a water-impermeable inner plastic zipper container 61 filled with ice chips 65. The ice bag device 31 containing the inner zipper container 61 can be attached, e.g., to the garments 82 and 83 using a plurality of safety pins 51, as is shown in FIG. 7 and FIG. 8. The safety pins 51 also provide the means to close the open end 35 of the outer cover 33.

FIGS. 4 and 5 are two views of an alternative embodiment of the ice bag device of the present invention, designated as 41, comprising the outer cover 43 in the open position containing ice 67 visible through the partly cut out portion of the outer cover 43. FIG. 4 is a perspective view of ice bag device 41. FIG. 5 is a cross-sectional view of the ice bag device 41 taken along the line 5-5. The liquid impermeable outer cover 43 has a sack structure with two sides 44 and 45 that are joined by three closed edges 46, 47, and 48, and one open side 49 with two edges 74 and 75. The outer cover 43 also has extended periphery 27 which is an extension from the closed edge 47 and extended periphery 29 which is an extension from the open edge 75, for use as the place for the safety pins to attach the ice bag device 41 to a garment. Side 44 comprises a water-impermeable plastic inner layer 441 which is laminated with an outer layer 442, and side 45 comprises a water-impermeable plastic inner layer 451 which is laminated with an outer layer 452. The inner layers 441 and 451 are provided with a pair of sealing strips 443 (male) and 453 (female) which are parallel and close to the top edges 74 and 75. One of the sealing strips, 443, is provided with a protruding rib and the other of these sealing strips, 453, is provided with a mating groove for receiving the rib in press-fit fashion to form a water tight seal. The sealing strips 443 and 453 are sealed tightly together once the outer cover 43 is filled with ice 67. In FIG. 4 the outer layer 442 is partly cut away to show part of the inner layer 441 and ice chips 67. The outer layers 442 and 452 are preferably made of sheet materials which can control the heat transfer, such as fabric or foam, in order to control the cooling rate, to avoid damage by overcooling, e.g., frostbite.

FIG. 6 is a view of the ice bag device 11 of FIG. 1 being attached to the outside of the back of the shirt 81 by a plurality of safety pins 51, with the outer cover 13 being partly cut away to show the ice-filled inner zipper bag 61 containing ice 65.

FIG. 7 is a view of the ice bag device 31 of FIG. 3 being attached to the inside of the jacket 82 by a plurality of safety pins 51, with the outer cover 33 being partly cut away to show the ice-filled inner zipper bag 61 containing ice 65.

FIG. 8 is a view of the ice bag device 31 of FIG. 3 being attached to the outside of the leg 83 of a pair of pants by a plurality of safety pins 51, with the outer cover 33 being partly cut away to show the ice-filled inner zipper bag 61 containing ice 65.

FIG. 9 is a view of an alternative embodiment of the ice bag device of the present invention designated as 91 comprising a flexible outer cover comprising a rectangular piece of flexible substrate 93, holding an inner reclosable zipper cooling container 61 containing ice chips 65, the ice bag device being attached to the outside of the back of the shirt 84 via the four extended peripheries 94, 95, 96, and 97 by a plurality of safety pins 51. The outer cover 93 is tied together with the garment surface using the safety pins 51 to form a closed compartment to enclose the inner zipper bag 61. In FIG. 9, the substrate 93 is partly cut away to show an inner plastic zipper container 61 which is filled with ice chips 65.

In general, it is important to promptly treat any trauma that damages the body so as to minimize the damage. Injuries like bruises, strains, etc., can be treated by the application of cold to minimize the damage. It is therefore useful to provide a means of treating such injuries promptly with cold.

In order to provide such means, one can either provide: (1) a non-constrictive ice bag device comprising a flexible ice bag outer cover which is filled with a cooling medium (when the cover is liquid impermeable) or at least one inner "cooling bag", or inner cooling pack, hereinafter simply "pack" or "packs", containing cooling medium, preferably said outer cover having an extended periphery on at least one side to permit attaching said outer cover, when it is assembled and filled with the cooling medium or at least one cooling pack containing cooling medium, to the inside or the outside of a garment using a plurality of safety pins, wherein "plurality" is typically from 1 to about 20 safety pins, such that said cooling medium is in close contact with an injured body part of an individual, without the need for a strapping and/or wrapping means, wherein said outer cover typically comprises a piece of flexible substrate, such as a piece of fabric, more preferably said outer cover being a sack structure (or pouch structure) with one or more open ends (or sides) and having two or more extended peripheries (or extended sides, or extended edges) that have a width of at least about 0.5 centimeter, more preferably of at least about 1 centimeter, and wherein said cooling medium is contained in either a resealable or sealed, typically flexible, typically plastic, liquid impermeable inner container to form an inner cooling pack, wherein said cooling medium is preferably either ice, ice and water combination, refrigeratable cooling gel, or endothermic chemical cooling system, wherein said inner cooling pack can be inserted through said open end(s) and/or side(s) of said outer cover, and wherein said open end(s) and/or side(s) are capable of being sealed to retain the said inner cooling pack using the said safety pins or the outer cover is sealable or sealed and comprises a liquid impermeable layer and the cooling media is inside the outer cover; (2) a non-constrictive ice bag device comprising a flexible outer cover for a cooling medium, having a layer of mounting adhesive to temporarily attach said cover, when it is filled with the cooling medium (when the cover is liquid impermeable) or one or more inner "cooling bags", or inner cooling packs, containing the cooling medium, to the inside or the outside of a garment, such that said cooling medium is in close contact with an injured body part of a user, without the need for a strapping and/or wrapping means, wherein the flexible outer cover is preferably a unitary structure, typically either a sack structure (or pouch structure) with one open end to receive one or more inner cooling packs, wherein each cooling pack comprises either a resealable or a sealed fluid impermeable, preferably plastic, container containing a cooling medium, or a closed sack structure containing one or more inner cooling packs, wherein each cooling pack comprises a permanently sealed fluid impermeable plastic container containing a cooling medium (In a preferred embodiment, the outer cover is self-adhering with the adhesive layer being an integral part of the outer cover and entirely or partially covering one side of the outer cover. In another preferred embodiment, the outer cover is not self-adhering, but with the adhesive layer being separated from the outer cover and being in the form of one or more adhesive strips, such as bandage adhesive strips or adhesive bandage strips, that are used to attach the outer cover to the garment. The adhesive layer is optionally, but preferably, covered with a release paper layer to protect the adhesive from prematurely sticking to a surface other than the intended user's garment.); and/or (3) an ice bag device comprising a flexible outer cover preferably being a unitary structure, typically either a sack structure (or pouch structure) with one open end or side, or a generally tubular structure with two open ends, with said open ends or sides optionally capable of being sealed, and having dimensions suitable to contain a cooling medium (when the cover is liquid impermeable), or one or more inner cooling packs or bags, wherein each said cooling pack can comprise a generally liquid impermeable container containing cooling media that can be inserted into said outer cover through said open end, and wherein said outer cover has a plurality of small apertures, wherein "plurality" is typically from 1 to about 40, preferably from about 2 to about 20, and more preferably from about 4 to about 10 small apertures, to permit the insertion of one, or more separate, string-like, members that can be used to attach the ice bag device, when it is assembled and filled with at least one cooling pack, to an injured body part of the user; and optionally, but preferably, to permit lacing one of the string-like members through the small apertures in both sides of the bag near each open end of the outer cover to close said open end.

The above covers are normally used to contain one or more inner cooling bags or packs containing a cooling medium. Each inner cooling pack comprises either a resealable or permanently sealed fluid impermeable plastic container containing a cooling medium, preferably either ice, water, ice and water combination, refrigeratable cooling gel, or endothermic chemical cooling mixture. However, if the outer cover is closed, it can contain one or more inner cooling packs, wherein each cooling pack comprises a permanently sealed fluid impermeable plastic container containing a cooling medium, preferably either refrigeratable cooling gel or endothermic chemical cooling mixture.

The above ice bag devices and covers can be used in methods in which first aid treatment of injuries is achieved by attaching the outer covers hereinabove holding one or more inner fluid impermeable plastic containers containing a cooling medium to an injured part, preferably by attachment to a garment so as to apply said cooling medium to an injured body part when the garment is worn. The covers are used in creating a non-constrictive ice bag device, preferably by providing said outer covers, filling one or more plastic zipper containers sealable by interlocking rib and groove sealing closure, with ice or an ice and water combination, placing the filled container(s) inside said outer covers, using safety pins, an adhesive layer, and/or string-like members to attach the assembled ice bag device to the injured part, preferably by attaching the cover inside or outside of a garment, such that said ice bag device is in close contact with an injured body part of the user. The inner cooling pack can comprise a resealable zipper container containing ice and/or an endothermic chemical system pack or a permanently sealed cooling pack containing ice or cooling gel, when such cooling pack is available.

It is important for first aid purposes to associate the covers, etc., with instructions for use to ensure that the method can be practiced efficiently, quickly, and effectively so as to maximize the effect of the cooling treatment on an injury. Preferably, the various parts are combined in an article of manufacture comprising the outer cover(s), optionally, one or more resealable or permanently sealed liquid impermeable containers for the cooling media, optionally, a sealed plastic wrapper to keep the outer cover and the optional elements in a hygienic, non-contaminated condition in storage, and preferably instructions for use. The article can also comprise safety pins and/or adhesive strips, and/or string-like members for purposes of attaching the cover(s) to a garment or a body part.

Safety pins or adhesive layer can be used to attach an ice bag device to a garment such that said ice bag device is in close contact with an injured body part of an individual when the garment is worn, and/or to close the opening of the outer cover of said ice bag device, but it is important to have a periphery which can be penetrated by the pins without puncturing the bag containing the cooling media. Similarly, if string-like members are to be used for attachment of the ice bag device, it is important to provide some small aperture(s) through which the string-like member can be threaded before tying the string-like member around the body part or forming a loop for attachment. Combinations of these attachment means can be used.

The cover(s) and the ice bag(s) are preferably compact, not bulky, preferably washable, and are optionally disposable.

The above description discloses, by way of example, some preferred embodiments of the present invention. However, persons of ordinary skill in the art are capable of creating numerous modifications within the scope of the claims. Changes in specifics of form and details can be made to the above-described embodiments. The claims and not the examples are the measure of the protected invention.

What is claimed is:

1. A flexible outer cover for an ice bag device, that is compact, not bulky, so that it can fit in a first-aid box along with other first-aid items, said cover being either a piece of flexible substrate or a sack structure with one or more open sides, having one or more extended peripheries for use to attach the outer cover to the inside or the outside of a garment by the use of a plurality of safety pins, wherein each extended periphery has a width of at least about 1 centimeter, and wherein said cover has dimensions to form one or more compartments suitable for containing one or more cooling packs which can comprise a generally liquid impermeable container capable of containing a cooling medium or which can contain cooling media when the cover is relatively liquid impermeable and sealable.

2. The outer cover of claim 1 wherein said cover has a generally rectangular or square configuration when flattened.

3. A flexible outer cover for an ice bag device, said cover being either a piece of flexible substrate or a sack structure with one or more open sides, having one or more extended peripheries for use to attach the outer cover to the inside or the outside of a garment by the use of a plurality of safety pins, wherein each extended periphery has a width of at least about 1 centimeter, and wherein said cover has dimensions to form one or more compartments suitable for containing one or more cooling packs which can comprise a generally liquid impermeable container capable of containing a cooling medium or which can contain cooling media when the cover is relatively liquid impermeable and sealable, wherein said cover has a generally rectangular or square configuration when flattened and wherein said cover has either a generally tubular structure having two opposite open ends, and wherein the cover has at least two extended peripheries from the two open ends or wherein said cover has a sack structure having three sealed sides and having the fourth side open, and wherein the cover has at least two extended peripheries, one extended periphery being at the open end and the other periphery being at the opposite side of the open end.

4. The outer cover of claim 3 wherein said cover has a sack structure having three sealed sides and having the fourth side open, and wherein the cover has at least two extended peripheries, one extended periphery being at the open end and the other periphery being at the opposite side of the open end.

5. The outer cover of claim 2 wherein said cover is a piece of substrate having extended peripheries on at least three sides.

6. The outer cover of claim 1 wherein said cover is made of material which is either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, and/or laminated materials.

7. An ice bag device comprising:
  (a) a flexible outer cover, said cover being either a piece of flexible substrate or a sack structure with one or more open sides, having one or more extended peripheries for use to attach the outer cover to the inside or the outside of a garment by the use of a plurality of safety pins, wherein each extended periphery has a width of at least about 1 centimeter, and wherein said cover has dimensions to form one or more compartments suitable for containing one or more cooling packs which can comprise a generally liquid impermeable container capable of containing a cooling medium or which can contain cooling media when the cover is relatively liquid impermeable and sealable.
  (b) at least one plastic liquid impermeable inner cooling container suitable for holding a cooling medium to form a cooling pack, wherein said inner container either is completely sealed and contains a cooling gel or water, or an endothermic chemical cooling system, or has one open side that can be closed by means of a resealable closure and contains ice or an ice and water mixture, and wherein said cooling packs have dimensions that enable them to fit inside the outer cover; and
  (c) from about 1 to about 20 safety pins.

8. The ice bag device of claim 7 wherein said inner container has a resealable rib and groove sealing closure and contains ice or an ice and water mixture.

9. The ice bag device of claim 8 wherein said inner container is a commercially available zipper bag.

10. The ice bag device of claim 7 wherein said ice bag device comprises from about 4 to about 12 safety pins.

11. A method for first aid treatment of injuries by using safety pins to attach the outer cover of claim 1 which holds an inner container containing a cooling medium to a garment to apply said cooling medium to an injured body part when the garment is worn.

12. A method of creating a non-constrictive ice bag device of claim 7 for attaching to the inside or the outside of a garment, such that said ice bag device is in close contact with an injured body part of the user when the garment is worn, by the steps of filling one or more plastic zipper containers with ice or an ice and water combination; placing the filled container(s) inside a flexible outer cover for an ice bage device, said cover being either a piece of flexible substrate or a sack structure with one or more open sides, having one or more extended peripheries for use at attach the outer cover to the inside or the outside of a garment by the use of a plurality of safety pins, wherein each extended periphery has a width of at least about 1 centimeter, and wherein said voer has dimensions to form one or more compartments suitable for containing one orm ore cooling packs which can comprise a generally liquid impermeable container capable of containing a cooling medium or which can contain cooling media when the cover is relatively liquid impermeable and sealable; and using a plurality of safety pins to attach the assembled ice bag device to the surface of the garment and optionally and additionally to seal said outer cover.

13. An article of manufacture comprising one or more flexible outer covers for an ice bag device, each of said covers being either a piece of flexible substrate or a sack structure with one or more open sides, having one or more extended peripheries for use to attach the outer cover to the inside or the outside of a garment by the use of a plurality of safety pins, ehrein each extended periphery has a width of at least about 1 centimeter, and wherein said cover has dimensions to form one or more compartments suitable for containing one or more cooling packs which can comprise a generally liquid impermeable container capable of containing a cooling medium or which can contain cooling media when the cover is relatively liquid impermeable and sealable, said covers being packaged in association with a set of instructions that tell an individual how to use the cover to assemble an ice bag device, how to use the product properly, and to ensure that the consumer knows what benefits can be achieved, and how best to obtain these benefits, wherein the instructions are in one language or multilingual, and wherein the instructions are in words, in illustrative images and/or icons, or in words in combination with illustrative images and/or icons.

14. The article of claim 13 further comprising one or more of: (1) the corresponding number of inner cooling containers to form cooling packs to be placed in the compartment(s) of the outer cover, wherein the cover can form one or more compartments, and wherein each cooling container is either an empty plastic zipper bag, refrigeratable gel pack, or chemical cool pack; (2) a plurality of safety pins; and/or (3) a sealed plastic wrapper to contain the outer cover, the inner cooling container(s), and/or the safety pins.

15. The article of claim 13 wherein said outer cover has dimensions suitable to contain one inner cooling pack.

16. The article of claim 13 wherein said set of instructions comprises one or more of the following instructions:
    (a) place the outer cover on a location either inside or outside of a garment such that the compartment(s) containing the cooling pack(s) is at the location in close contact with the injured area of the body when the garment is worn;
    (b) attach the outer cover to the garment using the safety pins, leaving one or more sides of the outer cover open to insert one or more inner cooling packs;
    (c) attach the outer cover to the inside of the garment if there is room inside the garment to fit the complete ice bag device and/or if the garment is composed of a thick layer, or attach the outer cover to the outside of the garment if the garment is made of thin material that allows good transmission of cold to the injured body part and/or if there is not enough room inside the garment;
    (d) fill one or more plastic zipper bags with ice and seal said bags for use as the inner cooling packs;
    (e) pre-cool one or more gel packs for use as the inner cooling packs;
    (f) activate one or more chemical cool packs for use as the inner cooling pack;
    (g) place the filled inner cooling pack(s) in the compartment(s) of the outer cover;
    (h) close the remaining open side(s) of the outer cover and attach the extended peripheries of said open side(s) to the garment using the same safety pins, by carefully piercing said peripheries so as to avoid puncturing the inner cooling pack(s); and/or
    (i) wear the garment to apply the resulting attached ice bag device over the injured part.

17. The article of claim 16 wherein said set of instructions further comprises one or more of the following instructions: (j) the instruction to direct the consumer to a source of ice, including a home refrigerator, ice boxes or ice coolers for beverages at a sport game, and/or a fast food restaurant and/or a hotel or motel on a trip; (k) the instruction to direct the consumer to keep an ice bag device in their first-aid kit; and/or (I) the instruction disclosing the non-constrictive nature of the ice pack herein when attached to a garment and/or the benefit of the non-constrictive nature.

18. An article of manufacture according to claim 13 wherein the set of instructions is printed on one or more of: the package, the wrapper, and/or an accompanying instruction flyer or booklet; and/or is communicated via print and/or electronic mass media, optionally selected from newspapers, magazines, radio, television, internet, circulars to members of sport and/or outdoor organizations, and combinations thereof.

19. An article of manufacture comprising one or more flexible outer covers according to claim 3, packaged in association with a set of instructions that tell an individual how to use the cover to assemble an ice bag device, how to use the product properly, and to ensure that the consumer knows what benefits can be achieved, and how best to obtain these benefits, wherein the instructions are in one language or multilingual, and wherein the instructions are in words, in illustrative images and/or icons, or in words in combination with illustrative images and/or icons, said article optionally further comprising one or more of: (1) the corresponding number of inner cooling containers to form cooling packs to be placed in the compartment(s) of the outer cover, wherein the cover can form one or more compartments, and wherein each cooling container is either an empty plastic zipper bag, refrigeratable gel pack, or chemical cool pack; (2) a plurality of safety pins; and/or (3) a sealed plastic wrapper to contain the outer cover, the inner cooling container(s), and/or the safety pins, wherein said article carries indicia on one or more of: the outer cover, the inner containers, the wrapper, the package, and/or the set of instructions, showing one or more of: a logo, emblem, symbol, motif, sign, figure, mark, icon, pictogram, insignia, design, image, description, and/or advertisement for one or more of: a sport league, sport franchise, sport sponsor, non-profit or governmental organization, and/or for-profit commercial or industrial organization.

20. The method of doing business wherein the article of claim 13 is distributed with the approval of one or more entities having an association with individuals that are likely to be injured and need an ice bag device on an urgent basis, said entity optionally being an amateur or professional athletic association and/or optionally, attaching the indicia of at least one of said entities to said article and/or associating said indicia with said article.

* * * * *